(12) United States Patent
Mulligan et al.

(10) Patent No.: US 7,970,466 B2
(45) Date of Patent: Jun. 28, 2011

(54) METHOD AND APPARATUS FOR OPTIMIZATION AND ASSESSMENT OF RESPONSE TO EXTRA-SYSTOLIC STIMULATION (ESS) THERAPY

(75) Inventors: Lawrence J. Mulligan, Andover, MN (US); D. Curtis Deno, Andover, MN (US); John E. Burnes, Andover, MN (US); Nirav V. Sheth, Coon Rapids, MN (US)

(73) Assignee: Medtronic, Inc., Minneapolis, MN (US)

(*) Notice: Subject to any disclaimer, the term of this patent is extended or adjusted under 35 U.S.C. 154(b) by 2141 days.

(21) Appl. No.: 10/680,494

(22) Filed: Oct. 7, 2003

(65) Prior Publication Data

US 2005/0075675 A1    Apr. 7, 2005

(51) Int. Cl.
*A61N 1/00* (2006.01)
*A61B 5/04* (2006.01)

(52) U.S. Cl. .......... 607/9; 607/18; 607/19; 607/23; 600/510

(58) Field of Classification Search .......... 607/9, 23, 607/18–19; 128/419; 600/510
See application file for complete search history.

(56) References Cited

U.S. PATENT DOCUMENTS

| | | | |
|---|---|---|---|
| 5,213,098 A * | 5/1993 | Bennett et al. | 607/18 |
| 5,441,525 A | 8/1995 | Shelton et al. | |
| 5,549,650 A | 8/1996 | Bornzin et al. | |
| 5,564,434 A | 10/1996 | Halperin et al. | |
| 5,628,777 A | 5/1997 | Moberg et al. | |
| 6,438,408 B1 | 8/2002 | Mulligan et al. | |
| 6,454,719 B1 | 9/2002 | Greenhut | |
| 2003/0074029 A1 * | 4/2003 | Deno et al. | 607/23 |
| 2004/0009235 A1 | 1/2004 | Li | |

FOREIGN PATENT DOCUMENTS

| | | |
|---|---|---|
| WO | WO0158518 | 8/2001 |
| WO | WO02053026 | 7/2002 |

\* cited by examiner

*Primary Examiner* — Niketa Patel
*Assistant Examiner* — Nicole F Lavert
(74) *Attorney, Agent, or Firm* — Stephen W. Bauer; Reed A. Duthler (57) ABSTRACT

A method and apparatus for optimizing and assessing the response to extra-systolic stimulation (ESS) are provided. An optimization/monitoring parameter is calculated as a function of potentiation ratio, PR, and recirculation fraction, RF, derived from measurements of myocardial contractile function during and after ESS. PR may be computed as the ratio of the contractile function on post-extra-systolic beats during ESS to baseline contractile function. RF may be computed as the slope of a linear regression performed on a plot of the contractile function for a post-extra-systolic beat versus the contractile function for the previous post-extra-systolic beat after ESS is ceased. The ESI resulting in a maximum optimization/monitoring parameter, preferably computed as the product of PR and RF, is determined as the optimal ESI. The operating ESI may be automatically adjusted, and/or PR and RF data may be stored for monitoring purposes.

20 Claims, 7 Drawing Sheets

METHOD AND APPARATUS FOR OPTIMIZATION AND ASSESSMENT OF RESPONSE TO EXTRA-SYSTOLIC STIMULATION (ESS) THERAPY

CROSS-REFERENCE TO RELATED APPLICATIONS

The present patent application hereby cross-references and incorporates by reference the entire contents of the following applications, each of which is filed on even date herewith: non-provisional U.S. application Ser. No. 10/680,528 entitled, "REFRACTORY PERIOD TRACKING AND ARRHYTHMIA DETECTION," now issued as U.S. Pat. No. 7,184,832, non-provisional U.S. application Ser. No. 10/680,462, entitled, "METHOD AND APPARATUS FOR CONTROLLING EXTRA-SYSTOLIC STIMULATION (ESS) THERAPY USING ISCHEMIA DETECTION," now abandoned, non-provisional U.S. application Ser. No. 10/680,493 entitled, "EXTRA-SYSTOLIC STIMULATION THERAPY DELIVERY AND SENSING VIA DIFFERENT ELECTRODE SETS," now abandoned, non-provisional U.S. application Ser. No. 10/680,695 entitled, "MULTIPLE PACING OUTPUT CHANNELS," now issued as U.S. Pat. No. 7,184,833, provisional U.S. application Ser. No. 60/509,204 entitled, "CARDIAC PACING MODALITY HAVING IMPROVED BLANKING, TIMING, AND THERAPY DELIVERY METHODS FOR EXTRA-SYSTOLIC STIMULATION PACING THERAPY," and provisional U.S. application Ser. No. 60/509,335 entitled, "SECURE AND EFFICACIOUS THERAPY DELIVERY FOR AN EXTRA-SYSTOLIC STIMULATION PACING ENGINE."

FIELD OF THE INVENTION

The present invention relates generally to the field of implantable cardiac stimulation devices and more specifically to a device and method for delivering extra-systolic stimulation to achieve post-extra-systolic potentiation in the treatment of cardiac mechanical insufficiency. In particular a device and method are provided for measuring a potentiation ratio and recirculation fraction for use in optimizing and assessing the response to extra-systolic stimulation.

BACKGROUND OF THE INVENTION

Cardiac myocytes stimulated with so-called paired, coupled, bi-geminal or intercalated pacing stimulation produce enhanced mechanical function on subsequent depolarizations of the heart. Herein, this type of cardiac pacing therapy is referred to as extra-systolic stimulation (ESS) which refers to delivery of cardiac pacing therapy soon after either an intrinsic or pacing-induced systole. The magnitude of the enhanced mechanical function is strongly dependent on the timing of the extra systole relative to the preceding intrinsic or paced systole. When correctly timed, an ESS pulse causes depolarization of the heart but the attendant mechanical contraction is absent or substantially weakened. The contractility of the subsequent cardiac cycles, referred to as the post-extra-systolic beats, is increased as described in detail in commonly assigned U.S. Pat. No. 5,213,098 issued to Bennett et al., incorporated herein by reference in its entirety. The mechanism for stroke volume augmentation and other effects of ESS therapy is thought to be related to the calcium cycling within the myocytes. The extra systole initiates a limited calcium release from the sarcolasmic reticulum (SR). The limited amount of calcium that is released in response to the extra systole is not enough to cause a normal mechanical contraction of the heart. After the extra systole, the SR continues to take up calcium with the result that subsequent depolarization(s) cause a large release of calcium from the SR, resulting in vigorous myocyte contraction.

As noted, the degree of mechanical augmentation on post-extra-systolic beats depends strongly on the timing of the extra systole following a first depolarization, referred to as the "extrasystolic interval" (ESI). If the ESI is too long, the effects of ESS therapy are not achieved because a normal mechanical contraction takes place in response to the extra-systolic stimulus. As the ESI is shortened, a maximal effect is reached when the ESI is slightly longer than the physiological refractory period. An electrical depolarization occurs without a mechanical contraction or with a substantially weakened contraction. When the ESI becomes too short, the stimulus falls within the absolute refractory period and no depolarization occurs.

One method for quantifying the effect of extra-systolic stimulation includes measuring a parameter indicative of myocardial contractile function on a pre-extra-systolic beat or beats and on a post-extra-systolic beat or beats and determining the ratio of these measures, which may be referred to as the "potentiation ratio" or "PR." The potentiation effect following an extra systole will generally persist for several post-extra-systolic beats before the contractile function returns to the baseline, pre-extra-systolic function. The rate of decay of the potentiation effect is referred to as the "recirculation fraction" or "RF." A return to baseline contractile function after a period of extra-systolic stimulation typically occurs within about six heart beats. However, RF may be higher or lower depending on the calcium handling properties of the myocardium which may be affected by the disease state of heart failure.

The above-cited patent to Bennett et al. generally discloses a paired pacing cardiac stimulator for the treatment of congestive heart failure or other cardiac dysfunctions. A cardiac performance index is developed from a sensor employed to monitor the performance of the heart, and a cardiac stress index is developed from sensor employed to monitor the cardiac muscle stress. Either or both the cardiac performance index and cardiac stress index may be used in controlling the delivery of PESP stimulation. Prior non-provisional U.S. patent application Ser. No. 10/322,792 filed 28 Aug. 2002, in which was issued into U.S. Pat. No. 6,738,667 on May 18, 2004, and corresponding PCT application (publication no. WO 02/053026) by Deno et al., which is hereby incorporated herein by reference in its entirety, discloses an implantable medical device for delivering post extra-systolic potentiation stimulation. PESP stimulation is employed to strengthen the cardiac contraction when one or more parameters indicative of the state of heart failure show that the heart condition has progressed to benefit from increased contractility, decreased relaxation time, and increased cardiac output PCT Publication WO 01/58518 (still pending) by Darwish et al., incorporated herein by reference in its entirety, generally discloses an electrical cardiac stimulator for improving the performance of the heart by applying paired pulses to a plurality of ventricular sites. Multi-site paired pacing is proposed to increase stroke work without increasing oxygen consumption and, by synchronizing the timing of the electrical activity at a plurality of sites in the heart, decrease a likelihood of development of arrhythmia.

As indicated in the referenced '098 patent, a possible confounding factor to broad utilization of ESS stimulation is potential for arrhythmia induction. If the extra-systolic pulse is delivered to cardiac cells during the vulnerable period, the risk of inducing tachycardia or fibrillation in arrhythmia-prone patients can increase. Thus, it is clear that an extra-systolic pulse must be delivered safely after the vulnerable period but within a limited window of time for achieving effective stroke volume augmentation and other effects of ESS therapy.

BRIEF SUMMARY OF THE INVENTION

Short-term benefits of such augmentation on cardiac function may be measured by assessing mechanical or hemodynamic heart function on post-extra-systolic beats, e.g. by measuring the PR. Maximizing contractile performance on post-extra-systolic beats may have a beneficial palliative effect on the short term but may or may not be curative in the scope of treating heart failure on the long-term. A preferred result would be both a measurable hemodynamic improvement and an actual reversal of the compensatory remodeling associated with heart failure. One change that occurs with heart failure progression is a depression of RF. An implantable device proposed for monitoring congestive heart failure includes measurement of RF as a parameter indicative of the state of heart failure as generally disclosed in U.S. Pat. No. 6,438,408, issued to Mulligan et al., hereby incorporated herein by reference in its entirety.

A need remains, however, for an implantable cardiac stimulation system and method that allows the ESI applied during extra-systolic stimulation therapies delivered for treating heart failure to be optimized with respect to the potentiation effect. Furthermore, a need remains for an implantable system and method that allows for assessment of the therapeutic benefit of extra-systolic stimulation with regard to the recovery or reversal of heart failure symptoms. Such methods will inherently regard both the short-term and long-term benefits of extra-systolic stimulation in optimizing and assessing the response to extra-systolic stimulation in the treatment of heart failure.

According to the present invention, an implantable cardiac monitoring/stimulation system and associated method are provided for optimizing and assessing the myocardial response to extra-systolic stimulation (ESS). The method includes measurement of a contractile function parameter based on a physiological sensor signal during post-extra-systolic cardiac cycles. Contractile function data are used in computing a PR and RF for one or more ESI settings. In one embodiment, PR is determined as the ratio of the contractile function determined from one or more post-extra-systolic beats during ESS at a particular ESI to the baseline contractile function measured when ESS is withheld. In another embodiment, a PR-like parameter is determined as the ratio of the contractile function determined from one or more post-extra-systolic beats during ESS at a particular ESI normalized by the contractile function determined during ESS at another ESI.

RF is determined from the rate of decay of the potentiation effect on post-extra-systolic beats. In one embodiment, contractile function is measured during a sequence of post-extra-systolic beats after ESS has ceased. RF is determined as the slope of a linear regression performed on a plot of the contractile function for a given post-extra-systolic beat versus the contractile function for the previous post-extra-systolic beat. In another embodiment, an RF-like parameter is determined by measuring the decay of the contractile function during progressively lengthened ESIs.

An ESI optimization and ESS monitoring parameter is then calculated for each of a number of test ESI settings as a function of the PR and the RF, f(PR,RF), computed for a given ESI setting. Preferably, the product of PR and RF (PR*RF) is calculated for a corresponding ESI setting. The ESI resulting in a maximum PR*RF product is selected as the optimal ESI. The operating ESI setting may be automatically adjusted to the optimal ESI. Alternatively or additionally, PR*RF, and/or PR and RF data along with an ESI, time and date label are stored for later retrieval for monitoring purposes.

The present invention is realized in a cardiac stimulation/monitoring system including an implantable device and a set of associated leads having at least a pair of pace/sense electrodes for sensing cardiac events and delivering ESS pulses and at least one physiological sensor for use in measuring myocardial contractile function. The device may further include other cardiac stimulation therapy capabilities and may be capable of monitoring a number of physiological parameters. The device may execute an optimization/monitoring procedure upon receipt of a manual command or on an automatic triggered or periodic basis to determine f(PR,RF) for one or more ESI settings. The device may thereby optimize the delivery of ESS by adjusting the operating ESI according to both enhanced mechanical function (PR) and an improved index of heart failure state (RF), both of which are taken into account by the optimization/monitoring parameter defined as a function of PR and RF. Furthermore, the state of heart failure and response to ESS may be assessed by storing the f(PR,RF) results, and desired supporting data, over time.

DETAILED DESCRIPTION OF THE PREFERRED EMBODIMENTS

The present invention is directed toward providing an implantable system for delivering an extra-systolic stimulation (ESS) cardiac therapy to achieve stroke volume augmentation, reduction in paced heart rate and the like, wherein the timing of and assessment of response to the electrical stimulation therapy, is controlled based on measuring PR and RF.

Figure 1:
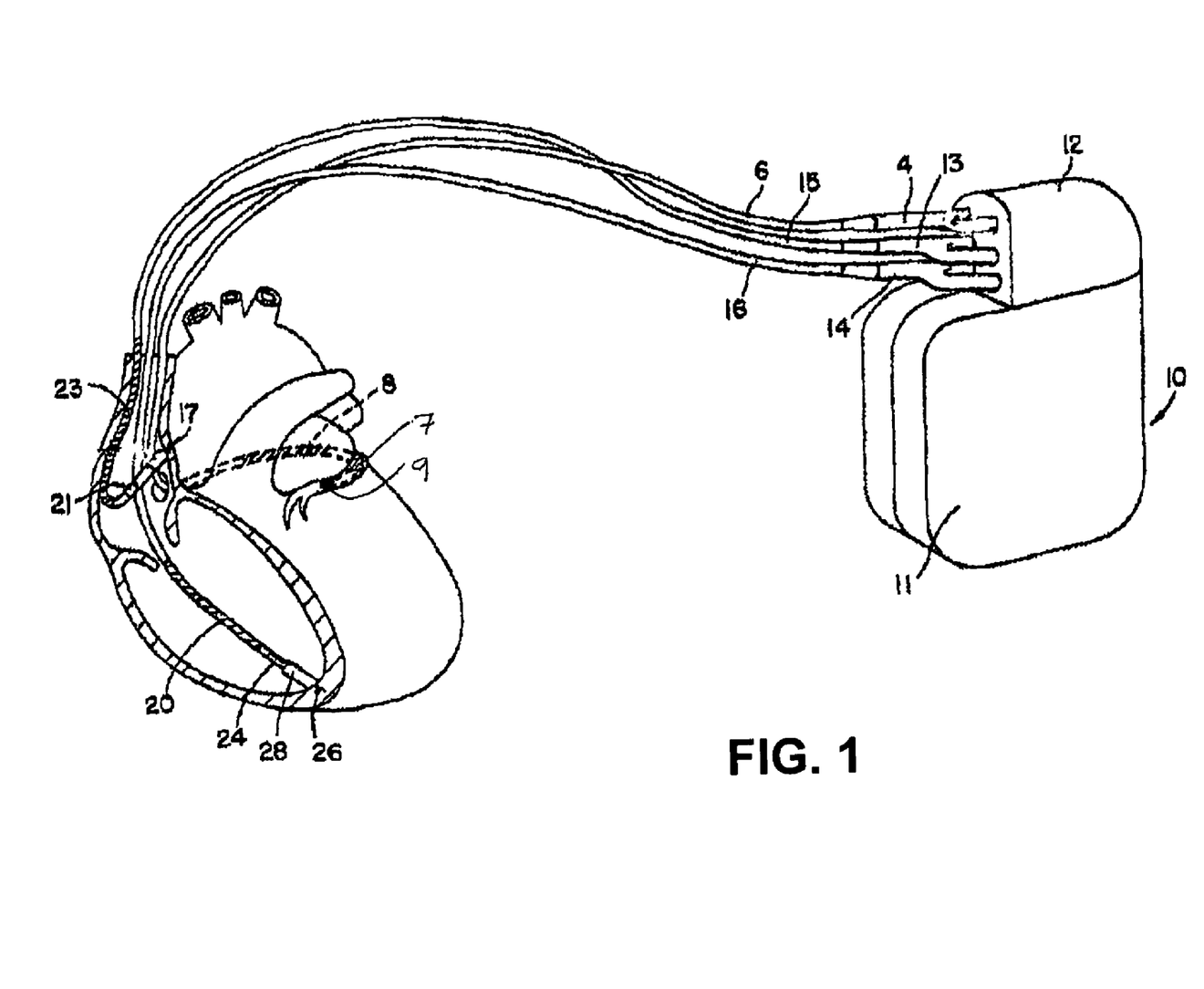
FIG. 1 is an illustration of an exemplary implantable medical device (IMD) in which the present invention may be implemented.

FIG. 1 is an illustration of an exemplary implantable medical device (IMD) in which the present invention may be implemented. IMD 10 is coupled to a patient's heart by three cardiac leads 6, 15, 16. IMD 10 is capable of receiving and processing cardiac electrical signals and delivering electrical stimulation pulses for ESS and may additionally be capable of cardiac pacing, cardioversion and defibrillation. IMD 10 includes a connector block 12 for receiving the proximal end of a right ventricular lead 16, a right atrial lead 15 and a coronary sinus lead 6, used for positioning electrodes for sensing and stimulating in three or four heart chambers.

In FIG. 1, the right ventricular lead 16 is positioned such that its distal end is in the right ventricle for sensing right ventricular cardiac signals and delivering electrical stimulation therapies in the right ventricle which includes at least ESS and may include cardiac bradycardia pacing, cardiac resynchronization therapy, cardioversion and/or defibrillation. For these purposes, right ventricular lead 16 is equipped with a ring electrode 24, a tip electrode 26, and a coil electrode 20, each of which are connected to an insulated conductor within the body of lead 16. The proximal end of the insulated conductors are coupled to corresponding connectors carried by bifurcated connector 14 at the proximal end of lead 16 for providing electrical connection to IMD 10.

In accordance with the present invention, at least one physiological sensor of mechanical or hemodynamic function is included in the IMD system. Such a sensor is used in providing a measure of myocardial contractile function during baseline rhythm and on post-extra-systolic beats during ESS for use in determining PR. Contractile function measurements are further used for measuring the decay of the potentiation effect on post-extra-systolic beats after ESS is ceased for computing RF.

A physiological sensor may be carried by any of the cardiac leads 6, 15, 16 or may be deployed on a separate lead. In the embodiment of FIG. 1, RV lead 16 includes a physiological sensor 28 for sensing a parameter relating to RV contractile function. Physiological sensor 28 may be provided, for example, as a pressure sensor or an accelerometer, or other type of implantable sensor, which may be used in measuring a parameter correlated to myocardial contractile function. In one embodiment, sensor 28 takes the form of a pressure sensor for measuring peak developed pressures or peak rate of pressure development (dP/dt) in a heart chamber. A pressure sensor may be embodied as generally disclosed in commonly-assigned U.S. Pat. No. 5,564,434 issued to Halperin et al., hereby incorporated herein by reference in its entirety.

In another embodiment, sensor 28 may take the form of a lead-based accelerometer for measuring wall motion, for example as generally disclosed in U.S. Pat. No. 5,628,777 issued to Moberg, or U.S. Pat. No. 5,549,650 issued to Bornzin et al., both of which patents are hereby incorporated herein by reference in their entirety. Other types of sensor which may be usefully employed for deriving a contractile function metric include, but are not limited to, blood flow sensors, acoustical sensors for measuring heart sounds, and impedance sensors for measuring heart chamber volumes.

The right atrial lead 15 is positioned such that its distal end is in the vicinity of the right atrium (RA) and the superior vena cava (SVC). Lead 15 is equipped with a ring electrode 21, a tip electrode 17, and a coil electrode 23 for providing sensing and electrical stimulation therapies in the right atrium, which may include atrial ESS and/or other cardiac pacing therapies, cardioversion and/or defibrillation therapies. In one application of ESS therapy delivery, extra-systolic stimulation is delivered to the atria to improve the atrial contribution to ventricular filling. The extra-systolic depolarization resulting from the atrial ESS stimulation pulse may be conducted to the ventricles for achieving the beneficial effects of ESS therapy in both the atrial and ventricular chambers. RA ring electrode 21, RA tip electrode 17 and SVC coil electrode 23 are each connected to an insulated conductor with the body of the right atrial lead 15. Each insulated conductor is coupled at its proximal end to a connector carried by bifurcated connector 13.

The coronary sinus lead 6 is advanced within the vasculature of the left side of the heart via the coronary sinus (CS) and great cardiac vein. The coronary sinus lead 6 is shown in the embodiment of FIG. 1 as having a defibrillation coil electrode 8 that may be used in combination with either the RV coil electrode 20 or SVC coil electrode 23 for delivering electrical shocks for cardioversion and defibrillation therapies. CS lead 6 is also equipped with a distal tip electrode 9 and ring electrode 7 for sensing functions and delivering ESS in the left ventricle of the heart as well as other cardiac pacing therapies. CS coil electrode 8, CS tip electrode 9 and CS ring electrode 7 are each coupled to insulated conductors within the body of lead 6, which provides connection to the proximal bifurcated connector 4. In alternative embodiments, lead 6 may additionally include ring electrodes positioned for left atrial sensing and stimulation functions, which may include atrial ESS and/or other cardiac pacing therapies.

In some embodiments, CS lead 6 may be equipped with a physiological sensor for measuring a signal related to myocardial contractile function, such as a pressure sensor or accelerometer as described above. It is recognized that a combination of physiological sensors located in one or more heart chambers may be used in deriving a parameter related to myocardial contractile function for the purposes of the present invention.

The electrodes 17 and 21, 24 and 26, and 7 and 9 may be used in sensing and stimulation as bipolar pairs, commonly referred to as a "tip-to-ring" configuration, or individually in a unipolar configuration with the device housing 11 serving as the indifferent electrode, commonly referred to as the "can" or "case" electrode. In addition, the coil electrodes 8,20,23 may be used to provide cardiac EGM recordings of myocardial activity. IMD 10 is preferably capable of delivering high-voltage cardioversion and defibrillation therapies. As such, device housing 11 may also serve as a subcutaneous defibrillation electrode in combination with one or more of the defibrillation coil electrodes 8, 20,23 for defibrillation of the atria or ventricles.

It is recognized that alternate lead systems may be substituted for the three lead system illustrated in FIG. 1. It is contemplated that ESS pulses may be delivered at one or more sites within the heart. Accordingly, lead systems may be adapted for sensing cardiac electrical signals and/or physiological signals related to contractile function at multiple cardiac sites and for delivering ESS pulses at the multiple sites, which may be located in one or more heart chambers.

While a particular multi-chamber IMD and lead system is illustrated in FIG. 1, methodologies included in the present invention may be adapted for use with other single chamber, dual chamber, or multichamber IMDs that are capable of sensing and processing cardiac electrical signals and delivering electrical stimulation pulses at controlled time intervals relative to an intrinsic or paced heart rate. Such IMDs may optionally include other electrical stimulation therapy delivery capabilities such as bradycardia pacing, cardiac resynchronization therapy, anti-tachycardia pacing, and preferably include arrhythmia detection and cardioversion, and/or defibrillation capabilities.

Figure 2:
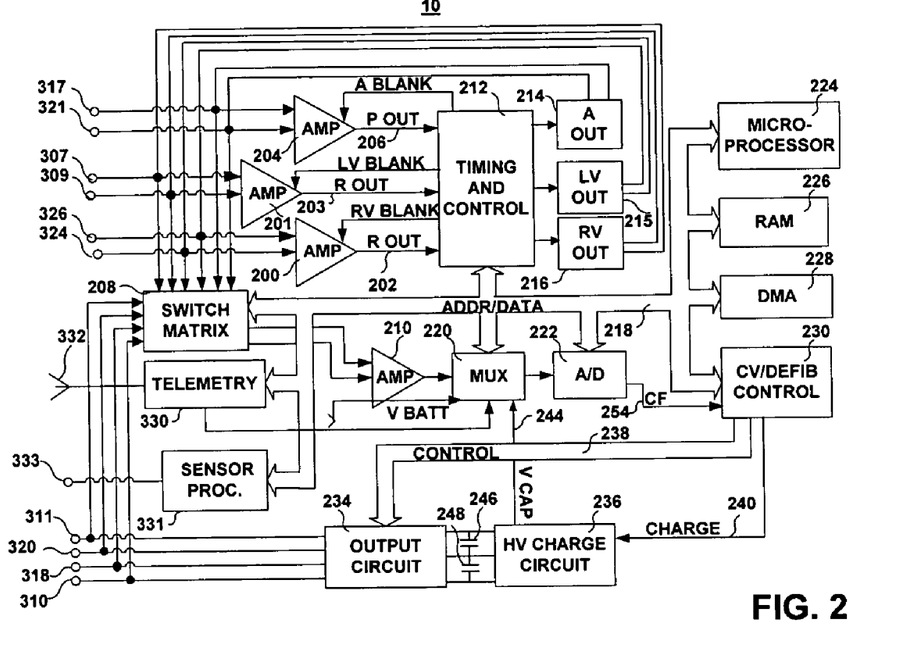
FIG. 2 is a functional schematic diagram of one embodiment of the IMD of FIG. 1.

A functional schematic diagram of one embodiment of IMD 10 is shown in FIG. 2. This diagram should be taken as exemplary of the type of device in which the invention may be embodied and not as limiting. The disclosed embodiment shown in FIG. 2 is a microprocessor-controlled device wherein the functions of IMD 10 are controlled by firmware and programmed software algorithms stored in associated RAM and ROM carried out by a central processing unit of a typical microprocessor core architecture. Another microprocessor controlled implantable device in which the present invention may be implemented is disclosed in the above-incorporated Mulligan patent. It is understood, however, that the methods of the present invention may also be practiced in other types of devices such as those employing custom integrated circuitry for performing specific device functions. As a result, the methods according to the present invention may be implemented as executable instructions stored on a computer readable medium.

With regard to the electrode system illustrated in FIG. 1, IMD 10 is provided with a number of connection terminals for achieving electrical connection to the leads 6, 15, 16 and their respective electrodes. The connection terminal 311 provides electrical connection to the housing 11 for use as the indifferent electrode during unipolar stimulation or sensing. The connection terminals 320,310,318 provide electrical connection to coil electrodes 20,8,23 respectively. Each of these connection terminals 311, 320,310,318 are coupled to the high voltage output circuit 234 to facilitate the delivery of high energy shocking pulses to the heart using one or more of the coil electrodes 8,20,23 and optionally the housing 11. Connection terminals 311,320,310,318 are further connected to switch matrix 208 such that the housing 11 and respective coil electrodes 20,8,23 may be selected in desired configurations for various sensing and stimulation functions of IMD 10.

The connection terminals 317 and 321 provide electrical connection to RA tip electrode 17 and RA ring electrode 21. The connection terminals 317 and 321 are further coupled to an atrial sense amplifier 204 for sensing atrial signals such as P-waves. The connection terminals 326 and 324 provide electrical connection to the RV tip electrode 26 and RV ring electrode 24. The connection terminals 307 and 309 provide electrical connection to CS tip electrode 9 and CS ring electrode 7. The connection terminals 326 and 324 are further coupled to a right ventricular (RV) sense amplifier 200, and connection terminals 307 and 309 are further coupled to a left ventricular (LV) sense amplifier 201 for sensing right and left ventricular signals, respectively.

The atrial sense amplifier 204 and the RV and LV sense amplifiers 200 and 201 preferably take the form of automatic gain controlled amplifiers with adjustable sensing thresholds. The general operation of RV and LV sense amplifiers 200 and 201 and atrial sense amplifier 204 may correspond to that disclosed in U.S. Pat. No. 5,117,824, by Keimel, et al. Generally, whenever a signal received by atrial sense amplifier 204 exceeds an atrial sensing threshold, a signal is generated on output signal line 206. P-waves are typically sensed based on a P-wave sensing threshold for use in detecting an atrial rate. Whenever a signal received by RV sense amplifier 200 or LV sense amplifier 201 that exceeds an RV or LV sensing threshold, respectively, a signal is generated on the corresponding output signal line 202 or 203. R-waves are typically sensed based on an R-wave sensing threshold for use in detecting a ventricular rate.

Switch matrix 208 is used to select which of the available electrodes are coupled to a wide band amplifier 210 for use in digital signal analysis. Selection of the electrodes is controlled by the microprocessor 224 via data/address bus 218. The selected electrode configuration may be varied as desired for the various sensing, pacing, cardioversion, defibrillation and ESS functions of the IMD 10. Signals from the electrodes selected for coupling to bandpass amplifier 210 are provided to multiplexer 220, and thereafter converted to multi-bit digital signals by A/D converter 222, for storage in random access memory 226 under control of direct memory access circuit 228. Microprocessor 224 may employ digital signal analysis techniques to characterize the digitized signals stored in random access memory 226 to recognize and classify the patient's heart rhythm employing any of the numerous signal processing methodologies known in the art.

The telemetry circuit 330 receives downlink telemetry from and sends uplink telemetry to an external programmer, as is conventional in implantable anti-arrhythmia devices, by means of an antenna 332. Data to be uplinked to the programmer and control signals for the telemetry circuit are provided by microprocessor 224 via address/data bus 218. Received telemetry is provided to microprocessor 224 via multiplexer 220. Numerous types of telemetry systems known for use in implantable devices may be used.

The remainder of the circuitry illustrated in FIG. 2 is an exemplary embodiment of circuitry dedicated to providing ESS, cardiac pacing, cardioversion and defibrillation therapies. The timing and control circuitry 212 includes programmable digital counters which control the basic time intervals associated with ESS, various single, dual or multi-chamber pacing modes, or anti-tachycardia pacing therapies delivered in the atria or ventricles. Timing and control circuitry 212 also determines the amplitude of the cardiac stimulation pulses under the control of microprocessor 224.

During pacing, escape interval counters within timing and control circuitry 212 are reset upon sensing of RV R-waves, LV R-waves or atrial P-waves as indicated by signals on lines 202,203,206, respectively. In accordance with the selected mode of pacing, pacing pulses are generated by atrial output circuit 214, right ventricular output circuit 216, and left ventricular output circuit 215 upon an escape interval time out. The escape interval counters are reset upon generation of pacing pulses, and thereby control the basic timing of cardiac pacing functions, which may include bradycardia pacing, cardiac resynchronization therapy, and anti-tachycardia pacing.

The durations of the escape intervals are determined by microprocessor 224 via data/address bus 218. The value of the count present in the escape interval counters when reset by sensed R-waves or P-waves can be used to measure R—R intervals and P—P intervals for detecting the occurrence of a variety of arrhythmias. In accordance with the present invention, timing and control 212 further controls the delivery of extra-systolic stimuli at selected extra-systolic intervals (ESIs) following either sensed intrinsic systoles or pacing evoked systoles. The ESIs used in controlling the delivery of extra-systolic stimuli by IMD 10 are preferably automatically adjusted by IMD 10 based on measurements of PR and RF as will be described in greater detail below. The output circuits 214, 215 and 216 are coupled to the desired stimulation electrodes for delivering cardiac pacing therapies and ESS via switch matrix 208.

The microprocessor 224 includes associated ROM in which stored programs controlling the operation of the microprocessor 224 reside. A portion of the memory 226 may be configured as a number of recirculating buffers capable of holding a series of measured R—R or P—P intervals for analysis by the microprocessor 224 for predicting or diagnosing an arrhythmia.

In response to the detection of tachycardia, anti-tachycardia pacing therapy can be delivered by loading a regimen from microcontroller 224 into the timing and control circuitry 212 according to the type of tachycardia detected. In the event that higher voltage cardioversion or defibrillation pulses are required, microprocessor 224 activates the cardioversion and defibrillation control circuitry 230 to initiate charging of the high voltage capacitors 246 and 248 via charging circuit 236 under the control of high voltage charging control line 240.

The voltage on the high voltage capacitors is monitored via a voltage capacitor (VCAP) line 244, which is passed through the multiplexer 220. When the voltage reaches a predetermined value set by microprocessor 224, a logic signal is generated on the capacitor full (CF) line 254, terminating charging. The defibrillation or cardioversion pulse is delivered to the heart under the control of the timing and control circuitry 212 by an output circuit 234 via a control bus 238. The output circuit 234 determines the electrodes used for delivering the cardioversion or defibrillation pulse and the pulse wave shape.

As noted with regard to FIG. 1, the implantable system preferably includes one or more physiological sensors 28 for monitoring a parameter indicative of myocardial contractile function. The physiological sensor may be a lead-based sensor as described with regard to the embodiment shown in FIG. 1 and reside within or on the heart, or endo- or extra-arterially for sensing a signal proportional to hemodynamic function or myocardial contractile function. Although depicted in FIG. 1 as residing near the apex of the RV, the sensor 28 may be disposed in any suitable location providing electrical and/or mechanical communication with said sensor 28. For example, the sensor 28 may comprise an accelerometer and may be coupled to a portion of a lead disposed within a cardiac vein. Such a location ensures that the sensor 28 can transduce left wall motion indicative of a variety of cardiac characteristics. For example, a sensor 28 coupled to the LV can provide a signal related to LV capture (for threshold testing or adjustment, chronic LV pacing, bi-ventricular optimization, etc.). Alternatively, a sensor, such as an acoustical sensor or impedance sensing electrodes, may be positioned on or within IMD 10. IMD 10 is additionally equipped with sensor signal processing circuitry 331 coupled to a terminal 333 for receiving an analog sensor signal. Sensor signal data is transferred to microprocessor 224 via data/address bus 218 for use in deriving contractile function parameters for use in computing PR and RF according to algorithms stored in memory 226. As will be described in greater detail below, computed PR and RF values are used in controlling the ESI during ESS such that an optimal mechanical enhancement of the post-extra-systolic beats, based on PR, is accompanied by an improvement in an index of heart failure state, based on RF. PR and RF values or a function of PR and RF, f(PR, RF), determined over time may be stored in recirculating buffers within memory 226 and made available for later retrieval for monitoring purposes. PR and RF data may be uplinked to an external device for review by a clinician via telemetry circuit 330. Such data may be useful to a clinician in managing the ESS therapy and monitoring the patient's clinical status. PR and RF data may be stored on a daily, weekly, monthly or other periodic basis.

Figure 3:
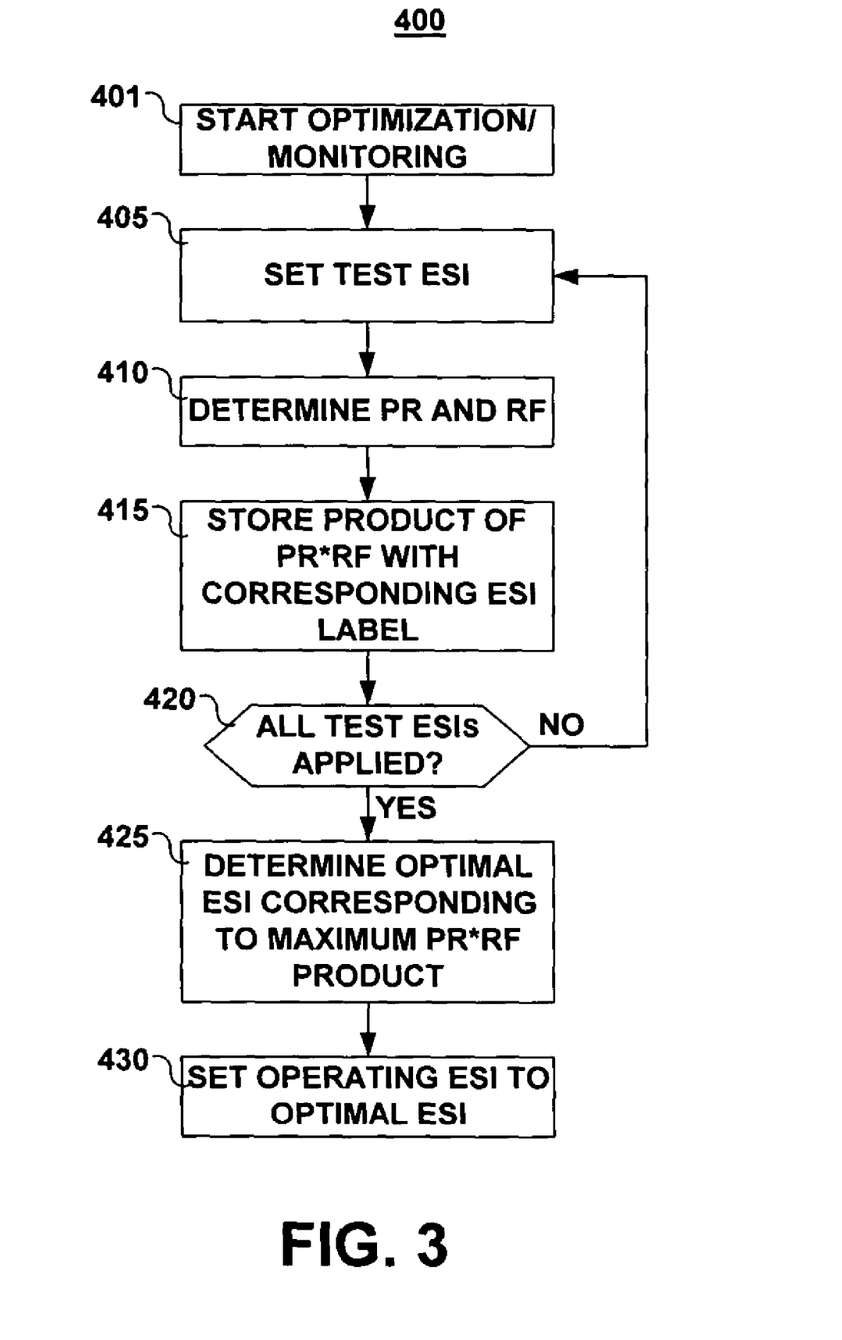
FIG. 3 is a flow chart providing an overview of methods included in one embodiment of the present invention for controlling and assessing ESS therapy based on measurements of PR and RF.

FIG. 3 is a flow chart providing an overview of methods included in one embodiment of the present invention for controlling and assessing ESS therapy based on measurements of PR and RF. At step 401, optimization/monitoring method 400 is initiated. Method 400 may be performed for optimizing the ESI used in delivering ESI. As such, operations included in method 400 may be initiated automatically, for example on a triggered or periodic basis, or manually by a clinician delivering a programming command using an external device. When performed on a periodic basis, optimization of the ESI may be performed on a daily, weekly or monthly basis or a more or less basis depending on the individual needs and the disease state of the patient. The optimization procedures included in method 400 may alternatively or additionally be initiated automatically on a triggered basis. For example following a detected physiological event such as an arrhythmia, a syncopal event, detection of cardiac-related disordered breathing, or other physiological events that may be monitored by the IMD 10, optimization method 400 may be performed to ensure maximal benefit of the ESS therapy under changing physiological conditions. A pacemaker with vasovagal syncope detection is generally disclosed in commonly assigned U.S. Pat. No. 5,441,525, incorporated herein by reference in its entirety. A method for determining the cardiac condition of a patient using the variability of a respiration parameter is generally disclosed in U.S. Pat. No. 6,454,719 issued to Greenhut, hereby incorporated herein by reference in its entirety.

Operations included in method 400 may also be performed for the sake of monitoring the myocardial contractile function, with or without automatic adjustments to the operating ESI setting. As will be described in greater detail below, PR and RF data, and in particular an optimization/monitoring parameter determined as function of PR and RF, f(PR,RF), may be gathered for monitoring purposes. As such, method 400 may be initiated manually or automatically, on a triggered or periodic basis, for acquiring PR and/or RF data for long-term storage. Such data are then available for later uplink to an external device for use in diagnostic, prognostic, or therapy management purposes.

At step 405, the initial ESI to be applied during optimization/monitoring method 400 is set by microprocessor 224. ESS pulses may be initially delivered at the currently programmed operating ESI, or at an initial test ESI setting, following paced and/or sensed cardiac events. During monitoring-only procedures, ESS may be delivered only at the programmed operating ESI so as to collect PR and RF data under the chronic operating conditions. Alternatively, during monitoring procedures and/or during optimization procedures, a number of test ESI settings over a range of intervals may be applied. During monitoring procedures, measurement of the PR and RF parameters over a range of ESIs may be of interest for evaluating the ESS therapy response and the heart failure state. During optimization procedures, a comparative analysis of the response to a number of ESIs will be performed to identify an optimal ESI.

The response to a particular ESI is measured by determining the PR and the RF as indicated by step 410. Methods for acquiring myocardial contractile function data for use in computing PR and RF will be described in greater detail below. Generally, PR is determined from a measure of myocardial contractile function during baseline rhythm and ESS. As indicated earlier, a contractile function parameter is preferably derived from a pressure sensor signal or an accelerometer signal, but may be derived from any sensor capable of generating a signal correlated to myocardial contractile function. In one embodiment, myocardial contractile function is measured according to a peak pressure signal or a peak rate of pressure development (dP/dt max). In other embodiments, myocardial contractile function is measured according to maximum wall acceleration measured by an accelerometer positioned in operative relation to the RV or LV, for example near the RV apex or on a coronary sinus lead, respectively. Derivation of a myocardial contractile function parameter based on pressure, wall motion, flow, volume, or acoustical signals may be performed according to any method known in the art.

A contractile function parameter is computed from a physiological sensor signal received during one or more cardiac cycles. In a preferred embodiment, a cardiac electrogram signal is used to define cardiac cycle boundaries, for example by measuring R—R intervals. Although it is possible to define cardiac cycle boundaries from mechanical signals, such as ventricular pressure, these signals may be less reliable during ESS because of the altered mechanical responses occurring during extra systoles and post-extra systoles.

Generally, the contractile function parameter is determined during baseline cardiac rhythm and during ESS at the currently applied ESI. The ratio of the contractile function parameter during ESS to the baseline contractile function parameter is calculated as the PR. Baseline function refers to the contractile function measured during a baseline cardiac rhythm when ESS is not being delivered. Other cardiac pacing therapies, such as bradycardia pacing or cardiac resynchronization therapy, may or may not be present.

Figure 4:
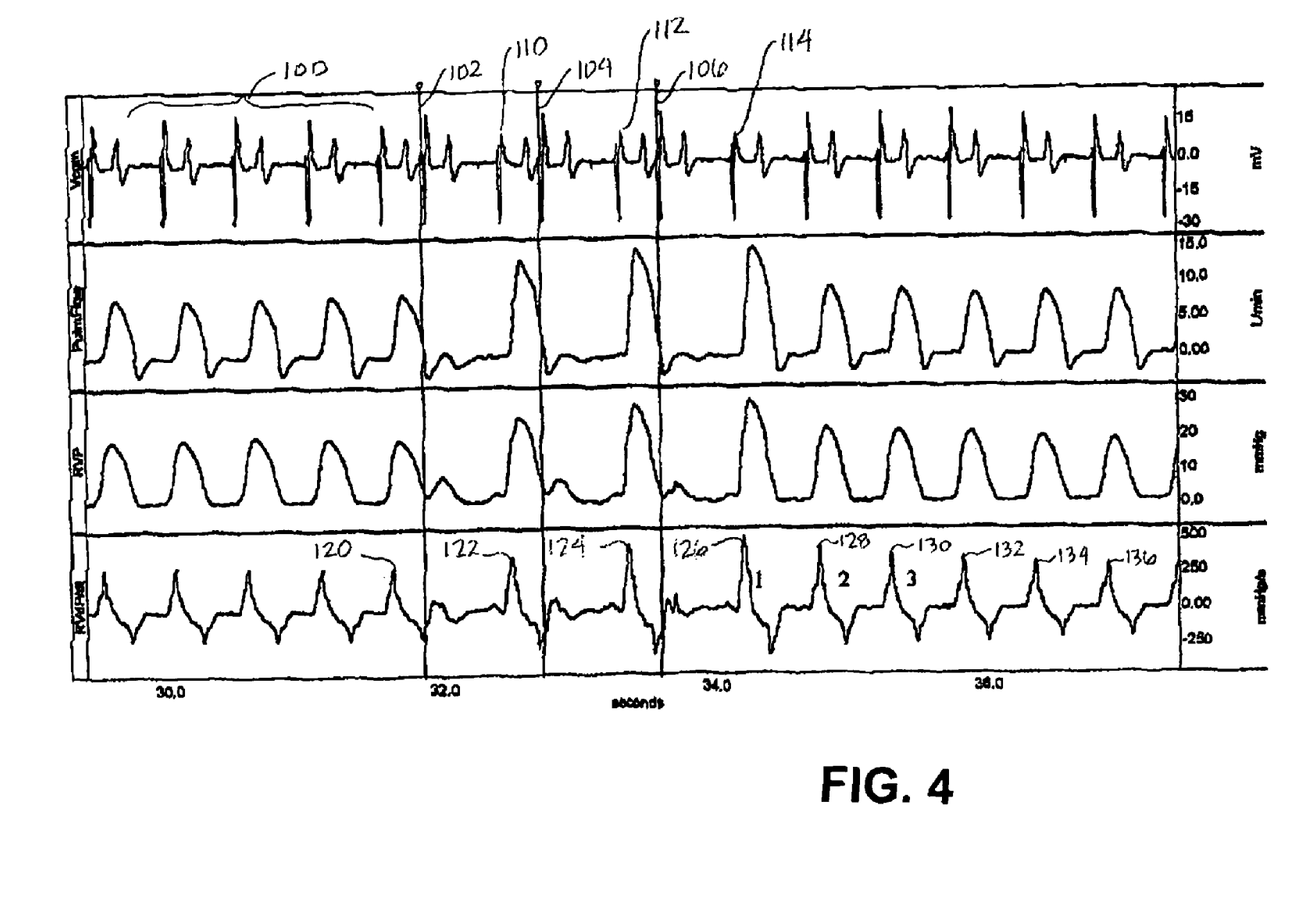
FIG. 4 is a plot of sample data measured during ESS during an animal study.

FIG. 4 is a plot of sample data measured during ESS during an animal study. The top line is the ventricular EGM showing a baseline cardiac rhythm 100 followed by three ESS pulses 102, 104 and 106 delivered after a sensed R-wave and the attendant ESI. The mechanical enhancement on the post-extra-systolic beats 110,112,114, each immediately following an ESS pulse 102,104,106, respectively, is notable on the second tracing depicting pulmonary blood flow, the third tracing depicting RV pressure, and the forth trace depicting RV dP/dt. The mechanical enhancement is seen to decay after ESS is ceased beginning with the first post-extra-systolic beat 114 after last ESS pulse 106. Subsequent peaks in RV dP/dt at 128, 130, 132, 134, 136 are observed to progressively decrease back toward the baseline RV dP/dt 120.

Contractile function, which may be measured as the peak pulmonary flow, RV pressure or RV dP/dt as shown in FIG. 4, is measured during the baseline cardiac rhythm 100 and on one or more post-extra-systolic beats 110, 112, 114 during ESS for determining PR. For example PR may be computed as the ratio of the peak RV dP/dt 122 following the first ESS pulse 102 to the peak RV dP/dt 120 of the last baseline cardiac cycle. Measurement of the decaying contractile function beginning with the first post-extra-systolic beat 114 after ESS is ceased is used in computing RF. For example the decaying peak RV dP/dt measured at 126, 130, 132, 134, 136 may be used in computing RF as will be described below. RF is believed to be a useful indicator of the state of heart failure and can provide an indication of the state of progression or regression of the heart failure through the comparison of RF data collected over time. RF may be measured as the time constant of the decay of the contractile function parameter following an extra systole. Reference is made to the previously-incorporated U.S. Pat. No. 6,438,408 issued to Mulligan et al., and to PCT Publication WO 02/053026. To measure the decay of the mechanical enhancement following an extra systole, a contractile function parameter is measured for at least two cardiac cycles following an extra systole. The contractile function parameter may be measured during a series of consecutive cardiac cycles encompassing a predetermined number of post-extra-systolic cardiac cycles, for example two to ten cardiac cycles. Alternatively, contractile function may be measured during each post-extra-systolic cardiac cycle until determination that the contractile function has returned to baseline. In yet other embodiments, the contractile function parameter may be measured from the first post-extra-systolic beat and an nth post-extra-systolic beat wherein the nth beat is predefined and may be, for example, the second to the eighth beat following an extra systole. The rate of decay may be estimated based on the difference in contractile function between the first and nth post-extra-systolic beats and the time interval or number of beats between them.

Figure 5:
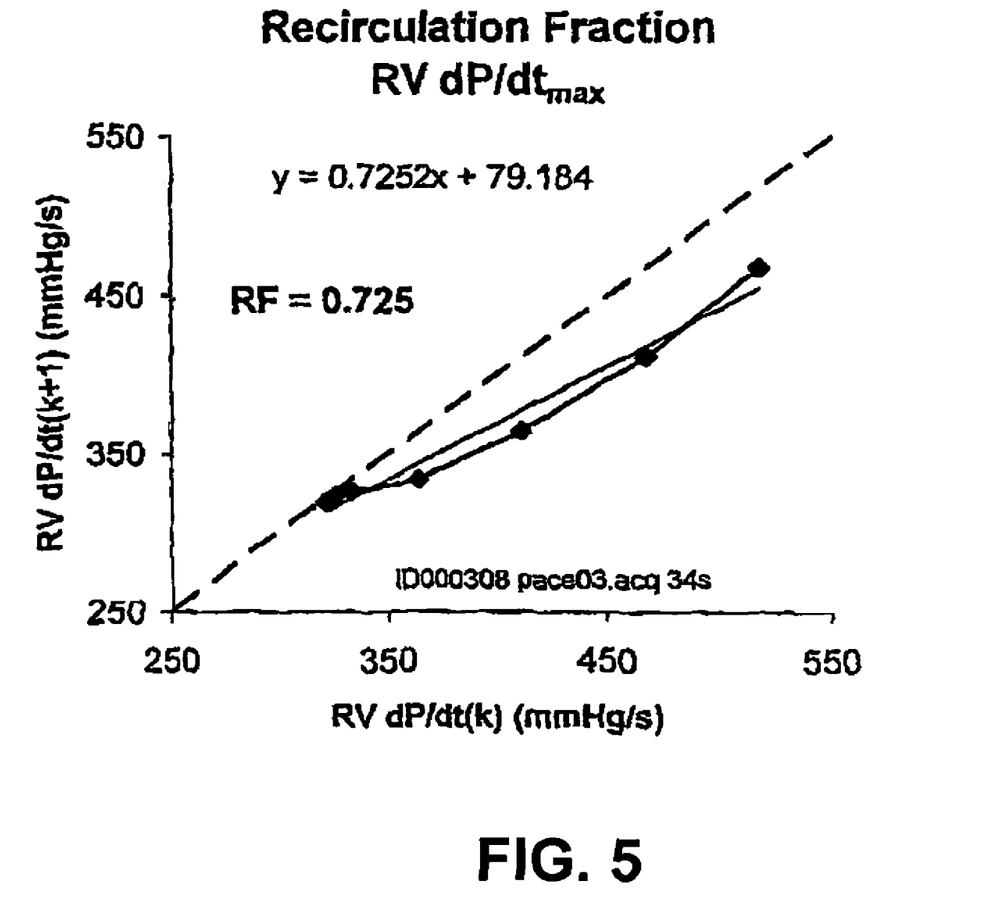
FIG. 5 is a graphic illustration of a method for determining RF from the decay of a contractile function parameter over a number of cardiac cycles.

FIG. 5 is a graphic illustration of a method for determining RF from the decay of a contractile function parameter over a number of cardiac cycles. RF is computed as the slope of the CF(k+1) versus CF(k) data wherein CF(k+1) is the contractile function parameter measured for the current post-extra-systolic cardiac cycle and CF(k) is the contractile function parameter measured for the previous post-extra-systolic cardiac cycle. In other words, the slope of the line defined by the equation:

$$CF(k+1)=RF*CF(k)+c, \quad (1)$$

wherein the slope is RF and c is a constant, may be determined by linear regression of the plotted post-extra-systolic contractile function data. In the example data plotted in FIG. 5, the slope of the line determined by linear regression is RF=0.725. Roughly 75% of the potentiation manifest on a previous beat is evident in the current beat. In this example, baseline contractile function, measured as RV dP/dt max, is approximately 320 mmHg/s from an anesthetized normal canine.

If desired, the RF may be converted to a time constant:

$$RF \text{ time constant}=-RR_0/ln(RF) \quad (2)$$

wherein $RR_0$ is the baseline RR interval (without extra systoles).

The RF time constant is representative of the time needed for the potentiated contractile function to decay to 1/e at the steady state heart rate.

Alternatively, the RF may be converted to a beat constant:

$$RF \text{ beat constant}=-[ln(RF)]^{-1} \quad (3)$$

The RF beat constant is representative of the number of cardiac cycles needed for the potentiated contractile function to decay to 1/e. For the example shown in FIG. 5, the beat constant is approximately 3 beats and the time constant is 1.6 seconds.

After determining the PR and RF at step 410 of FIG. 3, an optimization/monitoring parameter is computed as a function of PR and RF, f(PR, RF). Preferably, the product of the PR and RF is stored at step 415 with a label corresponding to the currently applied ESI along with time and date and any other pertinent information desired. The individual PR and RF values may also be stored such that PR and RF data is available to a clinician for review. At step 420, a determination is made whether all scheduled test ESIs have been applied. If all scheduled test ESIs have not yet been applied, method 400 returns to step 405 to set the next test ESI and repeat the determination of the resultant PR and RF at step 410.

Once all test ESIs have been applied, as determined at decision step 420, the optimal ESI is identified at step 425 as the ESI corresponding to the maximum product of the derived PR and RF data for each ESI. At step 430, the operating ESI may be automatically adjusted to be equal to the optimal ESI identified at step 425. ESS therapy may then be delivered at the optimal ESI until the next optimization procedure. Re-optimization of the ESI may be performed using method 400 on a periodic or event-triggered basis such that changes in a patient's condition that may cause changes in the response to ESS may be responded to in a timely manner.

A hypothetical set of PR and RF data is presented in TABLE I below. The PR and RF for each of a number of ESIs ranging from 200 ms to 320 ms are listed with the resulting PR*RF product. For this example, an ESI of 280 ms, corresponding to the maximum PR*RF product of 0.74, is considered optimal.

TABLE I

| ESI | PR | RF | PR*RF |
|---|---|---|---|
| 200 | 2.0 | 0.3 | 0.6 |
| 220 | 1.9 | 0.34 | 0.65 |

TABLE I-continued

| ESI | PR | RF | PR*RF |
|---|---|---|---|
| 240 | 1.8 | 0.38 | 0.68 |
| 260 | 1.7 | 0.42 | 0.71 |
| 280 | 1.6 | 0.46 | 0.74 |
| 300 | 1.5 | 0.46 | 0.69 |
| 320 | 1.4 | 0.46 | 0.64 |

Of note, a maximum PR occurs at the shortest ESI of 200 ms. Although this ESI may provide a maximum contractile function on post-extra-systolic beats with the attendant hemodynamic benefit, such a maximal contractile response sustained over long periods of time may prove undesirable. The depressed RF at this ESI setting, which results in a more abrupt drop in contractile function following termination of ESS, may be associated with a worsening of heart failure symptoms. A maximal mechanical enhancement of post-extra-systolic beats may not be optimal if coupled with a depressed RF. At ESIs greater than the optimal ESI of 280 ms, further increases in ESI result in a depressed PR without any beneficial increase in RF. The dependence of PR on ESI is well-known, and the long-term dependence of RF on ESI is postulated. Maintenance of a higher RF may be helpful in reducing or reversing heart failure symptoms.

Figure 6:
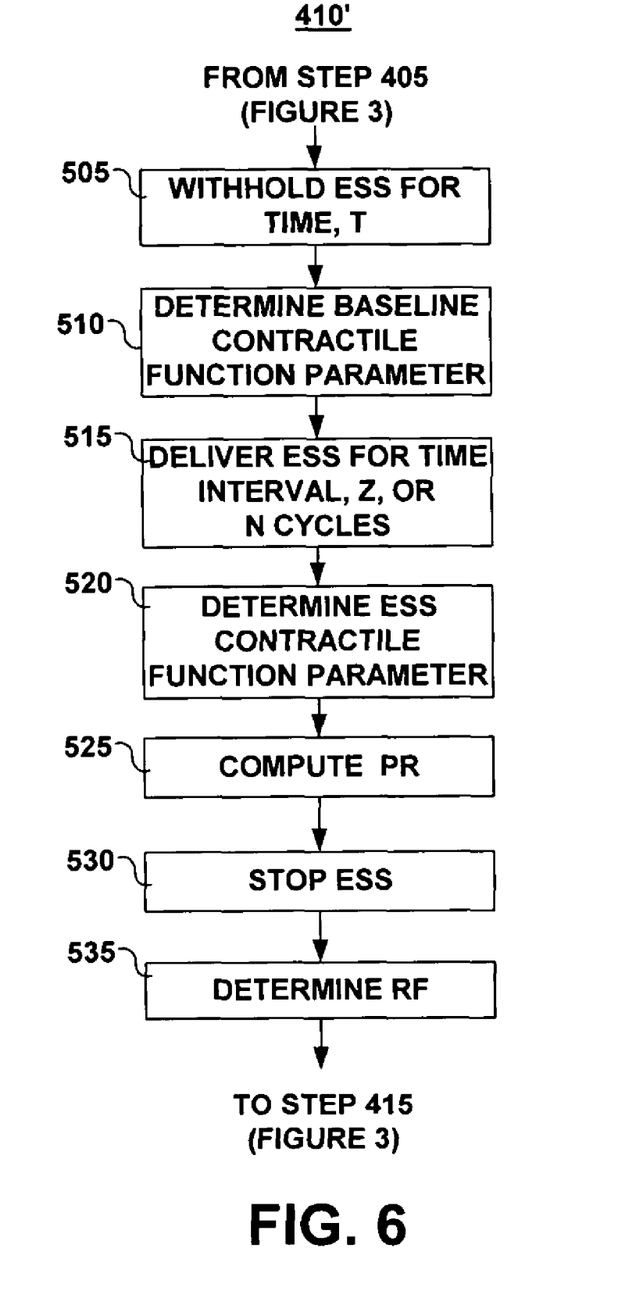
FIG. 6 is a flow chart summarizing the procedures that may be performed for determining PR and RF for a given ESI in one embodiment of the present invention.

FIG. 6 is a flow chart summarizing the procedures that may be performed for determining PR and RF at each applied ESI in one embodiment of the present invention. The steps shown in FIG. 5 represent a subroutine for acquiring the data needed to determine PR and RF for a given ESI at step 410 of the optimization/monitoring method 400 shown in FIG. 3. Subroutine 410' therefore follows step 405 of method 400, in which an initial test ESI is set. At step 505 of subroutine 410', ESS is withheld for a predetermined interval of time (Z) or number of cardiac beats (N). Preferably ESS is withheld for an amount of time adequate to reach steady-state baseline contractile function. Baseline contractile function may then be determined at step 510, absent any effects of a previous episode of ESS. It is expected that withholding ESS for at least 6 to 10 beats will allow the augmentation effect to substantially dissipate, however ESS may be withheld for up to several minutes or even hours. The baseline contractile function determined at step 510 is derived from a physiological sensor signal as described previously. The contractile function may be derived from the physiological sensor signal obtained during a single cardiac cycle or by averaging a contractile function parameter derived from the physiological sensor signal during a number of baseline cardiac cycles.

At step 515, ESS is initiated at the set ESI and sustained for a predetermined interval of time or number of cardiac cycles. ESS at the test ESI may be delivered for a single cardiac cycle or for several cardiac cycles, one or more minutes, or one or more hours. The contractile function during ESS at the currently set ESI is determined at step 520. The contractile function during ESS may be derived from a physiological signal obtained during a single post-extra-systolic cardiac cycle or by averaging the contractile function parameter derived from a number of post-extra-systolic cardiac cycles.

At step 525, the PR is computed by determining the ratio of the ESS contractile function determined at step 520 to the baseline contractile function determined at step 510. In one embodiment, PR is computed as the ratio of the contractile function parameter determined for the first post-extra-systolic beat during ESS delivery to the contraction function parameter determined for the last baseline rhythm beat prior to ESS initiation.

ESS is ceased at step 525 to allow a determination of the RF at step 530 by measuring the decay of the potentiation effect on beats following the last extra systole. RF may be determined in the manner described above and in conjunction with FIG. 5. Having collected the PR and RF values for the current test ESI setting, subroutine 410' is complete and method 400 of FIG. 3 proceeds to step 415 to compute and store the optimization/monitoring parameter defined as a function of PR and RF, e.g., the PR*RF product. This result is stored along with the corresponding ESI label, time and date information, and any other pertinent information desired.

Subroutine 410' is repeated for each ESI scheduled to be applied. Although redetermination of baseline contractile function for each ESI at step 510 is not required since an initial baseline contractile function may be used in all PR determinations, a period of baseline cardiac rhythm can be allowed to eliminate the potentiation effect from a previous ESS episode from influencing the PR and RF measurements on subsequent ESS episodes at different ESI settings.

Figure 7:
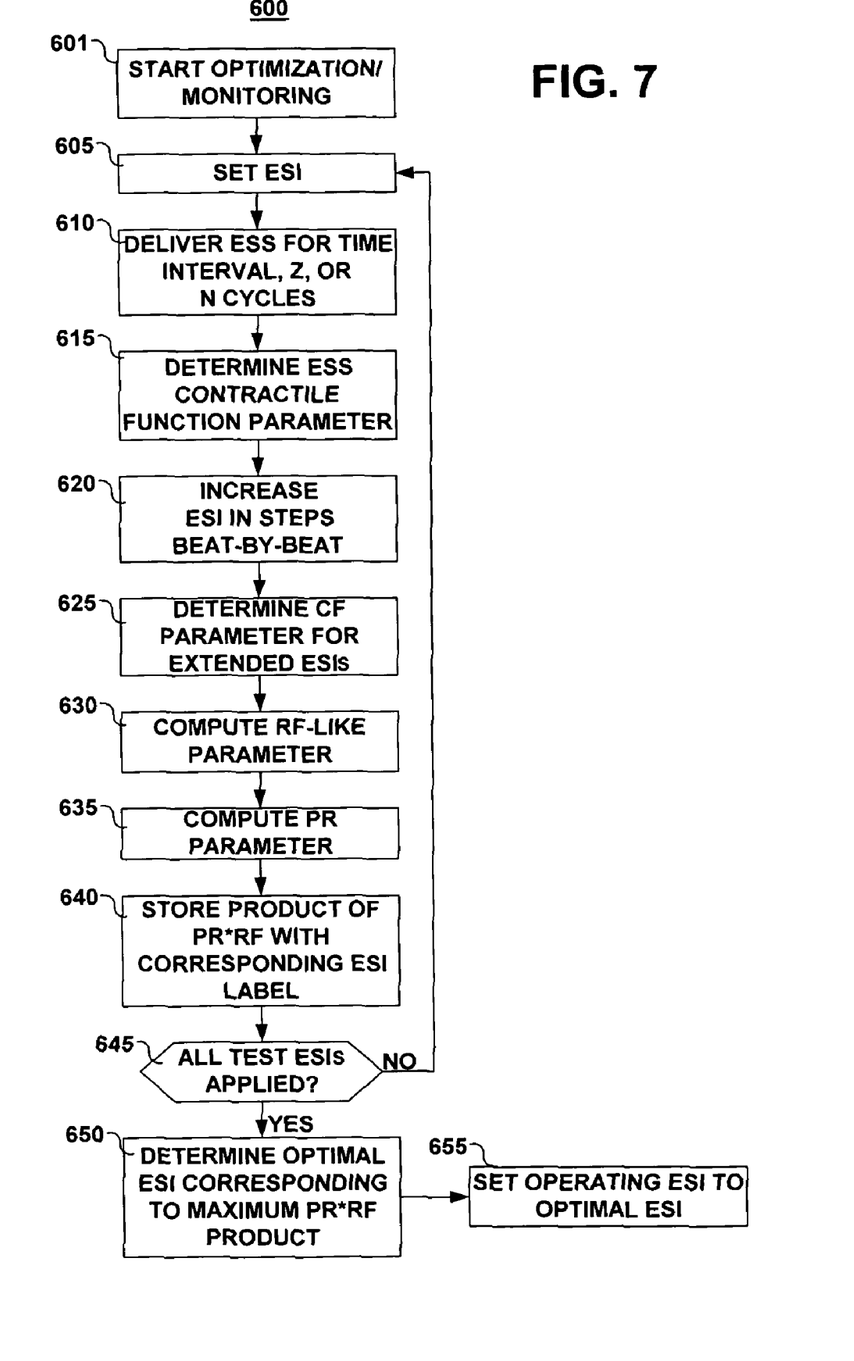
FIG. 7 is a flow chart summarizing the steps included in an alternative ESS optimization/monitoring method according to the present invention.

FIG. 7 is a flow chart summarizing the steps included in an alternative ESS optimization/monitoring method according to the present invention. Starting and stopping ESS during a monitoring/optimization procedure, as required by subroutine 410', may be undesirable due to the hemodynamic instability that may result. As such, a modification of the methods for collecting contractile function data for determining PR and RF may be made to allow continuous ESS during monitoring and/or optimization procedures. In method 600 the optimization/monitoring procedures are initiated at step 601, and an initial test ESI is set at step 605 in the manner described previously in conjunction with FIG. 3. At step 610, ESS is delivered at the initial test ESI for a predetermined interval of time (Z) or number of cardiac cycles (N). The contractile function is measured at step 615 during one or more post-extra-systolic cardiac cycles for use in computing PR.

At step 620, the ESI is increased beat-by beat in a step-wise fashion up to some maximum ESI. For example, the ESI may be increased by 10 to 20 ms per beat up to an ESI of 50 to 150 ms longer than the current test ESI setting. During the beat-by-beat increases in ESI, the contractile function is determined for each successive post-extra-systolic beat at step 625. The decay of the potentiation effect with progressively lengthened ESIs may then be computed as an RF-like parameter at step 630. Presumably, the decay in potentiation observed during increasing ESI will be proportional too or in correlation with the decay observed when ESS is ceased completely. In this case, the RF-like parameter is the slope of the equation:

$$CF(ESI_{i+j}) = RF*CF(ESI_i) + c \qquad (4)$$

wherein $CF(ESI_{i+j})$ is the contractile function of the post-extra-systolic beat following an ESS pulse delivered at an ESI increased by an increment j; $CF(ESI_i)$ is the contractile function of the previous post-extra-systolic beat which followed an ESS pulse delivered at the previous $ESI_i$, and wherein $ESI_i$ begins at the current ESI test setting and ends at some maximum ESI that is 50 to 150 ms longer than the current ESI test setting.

At step 635, a PR parameter is computed for the given test ESI. The PR parameter may be a ratio based on a previously determined baseline contractile function. Alternatively, a PR-like parameter may be determined as a ratio of the currently measured ESS contractile function to a selected normalization value. For example, the minimum or maximum contractile function measured during ESS at all test ESIs applied may be selected as a normalization value. Alternatively, contractile function measured during ESS at a particular ESI, for example the maximum ESI, which would presumably be closest in value to the contractile function of baseline rhythm may be selected as a normalization value. The ESI selected for determining the normalization value could be applied first in the order of scheduled test ESIs such that the normalization value is available for PR determination during application of subsequently scheduled test ESIs. The PR parameter determined for the first ESI would then have a value of 1. If the first ESI is the longest ESI scheduled for testing, the remaining PR values would be expected to have a value greater than 1 since the potentiation effect would be expected to be greater with shorter ESIs.

An optimization/monitoring parameter is computed as a function of PR and RF, f(PR,RF), and stored at step 640 as described previously. However, in method 600, f(PR,RF), which may be the PR*RF product, is computed from the RF-related parameter determined at step 630 and may use a PR-like parameter based on a selected normalization value rather than the baseline contractile function.

Steps 605 through 640 are repeated for each scheduled test ESI until all scheduled ESIs have been applied as determined at decision step 645. Hence, ESS is delivered continuously throughout these procedures with only the ESI being adjusted.

Once all test ESIs have been applied, the optimal ESI corresponding to a maximum PR*RF result, may be identified at step 650, and the operating ESI may be automatically adjusted to the optimal ESI at step 655. If method 600 is performed only for monitoring purposes, step 655 for adjusting an ESI setting may be omitted and the PR*RF results, along with supporting data, may be stored in a long-term memory buffer for later retrieval.

In embodiments that utilize a normalization value in the determination of a PR parameter that corresponds to a particular level of post-extra-systolic contractile function, for example a maximum or minimum contractile function, the contractile function data may be acquired and stored for all scheduled test ESIs before performing PR computations. Once contractile function measurements have been obtained for each ESI, the contractile function selected for normalization may be identified, and the PR computations performed. Hence, step 630 for determining the PR parameter for the currently applied ESI and step 640 for computing the PR*RF product, may alternatively be performed after application of all scheduled ESIs has been verified at step 645, such that contractile function data for all test ESIs are available for normalized PR-like parameter calculations.

Thus, a method and apparatus have been described for optimizing the ESI during ESS and for assessing the myocardial response to ESS based on the determination of a potentiation ratio (PR) parameter and a recirculation fraction (RF) parameter and functions thereof. While the embodiments described herein refer to a product of the PR and the RF for use as a parameter in the optimization and assessment of ESS therapy, other functions may be defined based on PR and RF or related parameters which may adequately reflect the short and/or long term dependence of these parameters on ESI.

Furthermore, while particular algorithms have been described herein for obtaining the contractile function measurements required for computing PR and RF related parameters, numerous variations to these algorithms may be made in which the net result of enabling computation of PR and RF related parameters for one or more ESI is obtained. While the computation of PR and RF and an optimization/monitoring parameter as a function of PR and RF has been described herein as operations performed online by the implanted device, it is contemplated that contractile function data may be stored by the implanted device and later uplinked for calculation and analysis of PR and RF data by an external device.

As described herein, aspects of the present invention may be beneficially employed in a cardiac stimulation device capable of delivering ESS therapy and optionally other types of cardiac stimulation therapies. However, it is understood that aspects of the present invention may also be usefully employed in devices intended for exclusively monitoring cardiac function, which utilize a physiological sensor of contractile function. The detailed embodiments described herein, therefore, are intended to be exemplary, not limiting, with regard to the following claims.

We claim:

1. A method of optimizing delivery of an extra-systolic stimulation (ESS) therapy for a plurality of extra-systolic intervals (ESIs), comprising:
    setting a test ESI for delivery of an ESS therapy;
    applying the ESS therapy at the test ESI;
    determining a potentiation ratio (PR) and a recirculation fraction (RF);
    storing the previously determined PR and RF with the test ESI;
    incrementing or decrementing the test ESI to a new value test ESI within a predetermined range of values and repeating the first four steps, wherein the new value test ESI is substituted for the test ESI;
    calculating a product of RF and PR for each test ESI;
    determining an optimal ESI that corresponds to a maximal product of RF and PR; and
    setting an operating ESI to the optimal ESI.

2. A method according to claim 1, further comprising performing the ESS therapy delivery in an implantable pulse generator.

3. Previously presented) A method according to claim 1, wherein determining PR and RF comprises deriving a contractile function from an output signal from a mechanical sensor.

4. A method according to claim 3, wherein the mechanical sensor comprises an accelerometer.

5. A method according to claim 4, further comprising disposing an accelerometer in mechanical communication with a ventricle.

6. A method according to claim 1, wherein determining PR and RF comprises deriving a contractile function from an output signal from a mechanical sensor disposed in fluid communication with a ventricle.

7. A method according to claim 6, wherein the mechanical sensor comprises a fluidic pressure sensor.

8. A method according to claim 7, further comprising disposing a fluidic pressure sensor in fluid communication with a right ventricle.

9. A method of optimizing delivery of an extra-systolic stimulation (ESS) therapy for a given extra-systolic interval (ESI), comprising:
    determining a baseline contractile function parameter when an ESS therapy is withheld or not delivered for a sufficient time or number of cardiac cycles for any related hemodynamic enhancement to substantially cease;
    delivering the ESS therapy for an interval of time or for a number of cardiac cycles;
    calculating an ESS therapy contractile function parameter during the delivery of the ESS therapy;
    calculating a potentiation ratio (PR) based on the baseline contractile function parameter and the ESS therapy contractile function parameter;

ceasing delivery of the ESS therapy;
determining a recirculation fraction (RF) for several cardiac cycles following the ceasing delivery of the ESS therapy; and
calculating a product of PR and RF.

10. A method according to claim 9, further comprising performing the ESS therapy delivery in an implantable pulse generator.

11. A method according to claim 9, wherein determining PR and RF comprises deriving a contractile function from an output signal from a mechanical sensor.

12. A method according to claim 11, wherein the mechanical sensor comprises an accelerometer.

13. A method according to claim 12, further comprising disposing an accelerometer in mechanical communication with a ventricle.

14. A method according to claim 9, wherein determining PR and RF comprises deriving a contractile function from an output signal from a mechanical sensor disposed in fluid communication with a ventricle.

15. A method according to claim 14, wherein the mechanical sensor comprises a fluidic pressure sensor.

16. A method according to claim 15, further comprising disposing a fluidic pressure sensor in fluid communication with a right ventricle.

17. A method according to claim 9, wherein determining the PR and RF further comprises deriving a contractile function from an output signal from a physiologic sensor, said physiologic sensor comprising a one of: a saturated oxygen sensor, a lactate sensor, a glucose sensor.

18. A computer readable non-transitory storage medium for storing instructions for optimizing delivery of an extra-systolic stimulation (ESS) therapy for a plurality of extra-systolic intervals (ESIs) comprising: instructions for setting a test ESI; instructions for determining a potentiation ratio (PR) and a recirculation fraction (RF); instructions for storing the previously determined PR and RF with the test ESI; instructions for incrementing or decrementing the test ESI to a new value within a predetermined range of values and repeating the first three steps; instructions for calculating a product of RF and PR for east test ESI; instructions for determining an optimal ESI that corresponds to a maximal product of RF and PR; and instructions for setting an operating ESI to the optimal ESI.

19. An apparatus for optimizing delivery of an extra-systolic stimulation (ESS) therapy for a plurality of extra-systolic intervals (ESIs), comprising:
means for setting a test ESI;
means for determining a potentiation ratio (PR) and a recirculation fraction (RF);
means for storing the previously determined PR and RF with the test ESI;
means for incrementing or decrementing the test ESI to a new value within a predetermined range of values and repeating the first three steps;
means for calculating a dot product of RF and PR for each test ESI;
means for determining an optimal ESI that corresponds to a maximal product of RF and PR; and
means for setting an operating ESI to the optimal ESI.

20. A method of monitoring the delivery of an extra-systolic stimulation (ESS) therapy during continuous delivery of the ESS therapy, comprising:
setting an extra systolic interval (ESI) to a test setting;
delivering the ESS therapy at the test setting for a number of cardiac cycles;
calculating an ESS therapy contractile function parameter during the delivery of the ESS therapy at the test setting;
adjusting the ESI to a next test setting;
delivering the ESS therapy at the next test setting for a number of cardiac cycles;
calculating the ESS therapy contractile function parameter for the next test setting during the delivery of the ESS therapy at the next test setting;
calculating a potentiation ratio parameter for the next test setting based on the first test setting contractile function parameter and the next test setting contractile function parameter;
adjusting the next test setting by a predetermined increment beat-by-beat for a number of cardiac cycles up to a maximum ESI,
calculating the ESS therapy contractile function parameter for each beat immediately subsequent to the adjusted next test setting; and
determining a recirculation fraction parameter in response to the ESS therapy contractile function parameters calculated for each beat corresponding to each of the adjusted next test settings;
setting the ESI to a second next test setting and calculating a potentiation ratio parameter and a recirculation fraction parameter for the second next test setting; and
determining an optimal ESI in response to a maximal product of the potentiation ratio parameter and the recirculation fraction parameter calculated for the next test setting and the second next test setting.

* * * * *